United States Patent [19]

Grischenko et al.

[11] Patent Number: 4,965,185

[45] Date of Patent: Oct. 23, 1990

[54] METHOD FOR LOW-TEMPERATURE PRESERVATION OF EMBRYOS

[76] Inventors: Valentin I. Grischenko, ulitsa Pushkinskaya, 67/69, kv. 31; Jury V. Kalugin, ulitsa Krasnoznamennaya, 6, kv. 24; Nina A. Luchko, ulitsa Dokuchaeva, 34; Elena N. Chernysh, ulitsa Chkalova, 13, kv. 26, all of Kharkov, U.S.S.R.

[21] Appl. No.: 209,632

[22] Filed: Jun. 21, 1988

[51] Int. Cl.$^5$ .............................................. A01N 1/02
[52] U.S. Cl. ......................................................... 435/1
[58] Field of Search ............................................ 435/1

[56] References Cited

U.S. PATENT DOCUMENTS

| | | | |
|---|---|---|---|
| 4,474,016 | 10/1984 | Winchell | 435/1 |
| 4,494,385 | 1/1985 | Kuraoka et al. | 435/1 |
| 4,688,387 | 8/1987 | Conaway | 435/1 |

OTHER PUBLICATIONS

Theriogenology, 1985, vol. 23, pp. 235 & 199.
Experimental Cell Research, vol. 89, No. 1, Nov. 1974, pp. 79-88.
Theriogenology, 1986, vol. 25, pp. 6-10.
Cryobiology-vol. 16, No. 1 (Feb. 1979), p. 6.

*Primary Examiner*—Sam Rosen
*Attorney, Agent, or Firm*—Ladas & Parry

[57] ABSTRACT

The method consists in cooling of embryos down to the temperature of the refrigerant in a buffer-salt fluid, the cooling process being carried out in a temperature diffusive powdered material that has preliminarily been cooled down to the refrigerant temperature. The buffer-salt fluid comprises a mixture of cryoprotectors, i.e., glycerol, dimethylsulphoxide, and a dihydric alcohol. An example of the temperature diffusive material is powdered metal.

7 Claims, No Drawings

METHOD FOR LOW-TEMPERATURE PRESERVATION OF EMBRYOS

The invention relates to cryobiology and is concerned with a method for cryopreservation of the embryos of mammals.

FIELD OF THE INVENTION

The present invention is applicable to deep freezing of embryos with the purpose of establishing a low-temperature bank of embryos of vanishing and rare animal spices. Additionally, the present invention is applicable to the establishment of a bank for maintaining genetically valuable strains of mice whose utilization is concerned with advances in further development of reproductology, theriogenology, pharmacology, immunology, virology, and experimental-and-clinical medicine.

The invention can also find application in other fields of cryobiology, e.g., in public health service where successful embryo implantation to a female patient is the most radical antisterility measure, while transplantation of ovarian tissue serves an efficacious method for correction the general hormonal status of a patient in a number of disease of various etiology. In addition, perfusion of embryonal bone marrow possessing reduced immunogenicity is a promising means in treatment of hemopoiesis suppression in female patients. The aforementioned therapeutic measures involve an adequate amount of appropriate biologic material which is attainable only when its prolonged storage in a deeply frozen state is practised.

The invention is also applicable in farming practice, where cryopreserved embryos have found widespread use for breeding noval races of farm animals, in commercial stock-raising, and in fish-farming for cryopreservation of fish embryos, especially of sturgeons and carps.

Thus application of low temperatures and particularly deep refrigeration for storage of embryos after their isolation from an organism, is covering still greater domains of man's economic activity, public health protection inclusive.

At present the trend towards establishment of low-temperature banks for storage of genetic resources has gained widespread development, particularly, those for storage embryos of commercially valuable farm animals with a view to intensifying animal husbandry.

Extensive use of mammals' embryos in medical practice and animal husbandry has rendered stringent requirements upon transplantation material whose quality is critical to the final result of transplantation procedure which is necessary for combatting sterility and for acceleration breeding of highly productive farm animals.

However, the heretofore developed methods for cryopreservation of embryos fail to provide high-level preservation of the cells which results in great losses of valuable biologic material. Experiments on cryopreservaton of embryos show that their optimization is concerned with a possibility of the vitrification development in the biological specimen being frozen at single stage ultrahigh rate cooling.

DESCRIPTION OF THE PRIOR ART

Known in the art is a method for freezing mouse embryos in a medium of 1.0 M dimethylsulphoxide (DMSO) incorporating initiation of crystallization at $-3.5°$ C. and cooling at a rate of 0.2 to $2.0°$ C./min down to $-40°$ C. followed by immersion in a refrigerent, i.e., liquid nitrogen. Survival rate of the embryos after their thawing equals 65 percent (cf. Experimental Cell Research, v. 89, No. 1, 1974, S.P. Leibo, P.M. Mazur, S.C. Jackowsky. 'Factors affecting survival of mouse embryos during freezing and thawing', pp. 79–89).

A disadvantage of this method resides in low survival rate of embryos that have undergone cryopreservation and badly affected results of freezing in response to most negligible deviations of the freezing thawing process parameters from optimal values.

One more prior-art method for cryopreservation of mouse embryos in a phosphate-salt buffer (PBS) containing 1.45 M of DMSO is known. According to the method the cryoprotectore is introduced into and withdrawn from the embyos dropwise, the cooling rate is $0.3°$ C./min, the survival rate, 67 to 68 percent.

The aforesaid method suffers from low survival rate of the embryos involved, poor reproducibility of the method, manual control of the cooling procedure, a great number of movable components in the equipment which complicates synchronization of crystallization process control and affects reproducibility of the results. Among other disadvantages of the process are long duration of the cryopreservation cycle, as well as complexity and high labor consumption of work performed (cf. Cryobiology, v. 16, 1979. G.H. Reilmaker, C.M.P.M. Verhamme. 'A simplified method for freezing mouse embryos', pp. 6–10).

Another method for cryopreservation of mouse embryos in a medium of 2.0 M glycerol plus 0.5 M saccharose is known. After a 15-min incubation the embryos were placed in a polystyrene tube having an inside diameter of 4 mm, which, after having been hermetically sealed, was immersed in liquid nigtrogen. Survival rate of the thus-treated embryos was equal to 84 percent.

A disadvantage of the method is the development of the crystallization, high osmotic activity responsible for latent damgage to the cells which tells unfavourably on their development in a culture medium after thawin. A too low cooling rate (about $20°$ C./min) concerned with formation of a thermoinsulation shell round the tube, contributes to the development of the crystallization process and affects the probability of vitrification of the liquid portion of the cryobiologic system. (cf. Theriogenology, v. 23, No. 1, 1985, T.J. Williams, S.E. Tohnson. "Quick-freezing of day four mouse embryos"p. 235).

Still one more method for cryoconservation of mouse embryos in a medium of 3.5 M glycerol mixed with 0.5 M saccharose is known in the present state of the art. Upon fractional addition of the cryopreservative to the cells the latter were placed in polystyrene tubes which, after having been hermetically sealed, were immersed in liquid nitrogen, whereby the survival rate of the thus-treated embryos is equal to 85 percent.

Among the disadvantages of the abovementioned method are too high concentration of osmotically active substances in the cryopreservative and low cooling rate of the embryos, which is causative of latent injuries of the cell membrane and affects adversely subsequent development of the embryos in a culture medium after thawing (cf. Theriogenology, v. 25, No. 1, 1986, K.A. Biery, G.E. Seddel Jr., R.P. Elsden, "'Cryopreservation of mouse embryos by direct plunging into liquid nitrogen', p. 140).

A further method for cryopreservation of embryos is known, wherein the embryos isolated from the organism of a mouse were placed in a polystyrene tube in a medium of 1.4 M glycerol and 1.1 M saccharose, the tube was hermetically sealed at both ends, and the cells were left in the tube for 25 to 30 minutes. (cf. Theriogenology, v. 23, No. 1, 1985. K.T. Krag, I.M. Koehler, R.W. Wright. 'A method for freezing early murine embyos by plunging directly into liquid nitrogen', p. 199).

Thereafter the tubes were immersed in liquid nitrogen. Thawing was carried out at 37° C. The tube contents were poured out into Petri dishes and washed thrice in a few portions of 0.5 M saccharose, whereupon they were cultivated in a nutrient medium. From 40 to 67 percent of the thawed-out embryos developed to the blastocyst stage. High concentrations of the cryoprotectors such as glycerol which penetrate poorly into the embryos, and saccharose that does not penetrate therein altogether, are aimed at dehydration of the cells in order to establish backgrounds for their vitrification after a quick cooling (at a rate of about 20° C./min).

The method in question suffers from low results owing to too high concentration of cryopreservatives in the cryoprotective medium, which cryoprotectors even when added fractionally, in three steps, to the embryos are responsible for their damge due to osmotic factors. With a total concentraton of the cryopreservatives applied equal to 48.6 percent, toxic effect of the cryooprotective compounds on the embryos is not out of the question. Apart from all mentioned above, the rate of cooling of the embryos obtained due to their direct plunging into liquid nitrogen is inadequately high for vitrification to develop, even in case of high concentratoin of cryopreservatives, snce a thermal-in-sulating shell formed between the tube and liquid nitrogen and consisting of nitrogen vapour, impedes high-rate heat withdrawal from the embryos being treated.

OBJECTS AND SUMMARY OF THE INVENTION

It is an object of the present invention to provide a higher survival rate of embryos upon their low-temperature preservation.

It is another object of the present invention to provide a simpler method for low-temperature preservation of embryos.

It is one more object of the present invention to make the method for low-temperature preservation of embryos less expensive.

It is still another object of the present invention to substantially cut down the time spent for low-temperature preservation of embryos and to considerably add to labour procuctivity.

The foregoing objects and advantages of the present invention are accomplished due to the fact that in a method for low-temperature preservation of embryos, incorporating their cooling down to the refrigerant temperature in a buffer-salt fluid which comprises a cryoprotector, i.e.,glycerol, according to the invention, cooling is carried out in a temperature diffusive powedered material which has preliminary been closed down to the temperature of the refrigerant, while the buffer-salt liquid also contains cryoprotectors, i.e., dimethylsulphoxide (DMSO) and a dihydric alcohol.

The herein-proposed method for low-temperature preservation of embryos is instrumental in higher survival of the embryos involved due to their cooling with the aid of a temperature diffusive powdered material, which makes it possible to attain as high cooling rate as a few scores of thousands of degrees per minute, which results in that the vitrification process is developed in the embryos being treated.

Moreover, the method proposed herein makes it possible to reduce the afflicting intensity of the injurious effect produced by recrystallization on the biological structures of the embryos during their thawing, this being attained due to incorporation of a cryoprotector, viz., DMSO and a dihydric alcohol into the cryopreservative forumulation, both serving as an antisalt buffer preventig migration of the crystals and ensuring against their increase in size that adds to the hydrate shell round the biomacromolecules and catalytic centres of proteins.

The applied cryoprotectors are of three kinds, having different degrees of permeation of the cell membrane (glycerol, DMSO, or one of the derivatives of a dihydric alcohol) taken in a low toatl concentration (14.75 to 15.25 percent) and cause no osmotic injuries or toxicity development. Also, at the same time promoting vitrification and affording comprehensive protection to the embryos in the course of cryoprotection and thawing. Besides, the mixture of the cryopreservatives used in withdrawn without afflicting damage to the cells.

The proposed method makes it possible to substantially simplify the process of low-temperature preservation of embryos due to its being composed of a minimum complex of simplest operations that do not involve special professional skill on the part of the operator.

This, in turn, makes it possible to considerably cut down the time required for carrying out the entire cycle of low-temperature preservation due to curtailed number of operations and the time spent for each of these, where the method becomes much more efficient and less expensive.

In a preferred embodiment of the present invention zinc is used as the temperature diffusive powdered material.

Selection of such a powdered material is accounted for by its high thermal conductivity as compared with some low-expensive powdered materials, which provides for high cooling rate of embryos.

It is expedient that 1,2-propanediol be used as the dihydric alcohol, while its mixture with DMSO is selected in view of the fact that DMSO is effect a cryoprotector that most readily permeates into the embryonic cell and affords protection to the endocellular biologic structures during freezing and thawing. Use of 1,2-propanediol enables not only the endocellular structures of the embryo to be successfully protected but also its membrane apparatus, this being due to an average permeation rate of said alcohol as compared with the other cryoprotectors employed in the method.

According to one of the embodiments of the present invention, with liquid nitrogen used as the refrigerent, each of the three cryoprotectors is taken in a concentration lying within 4.75 and 5.25 per cent. When taken in the aforesaid concentrations the cryoprotectors exhibit their cryoprotective properties most effectively, are practically nontoxic and feature not inconsiderable osmotic properties.

In an alternative embodiment of the present invention each of the crypoprotectors is taken in a 1:1 ratio. Such a ratio enables one to breed hope for equal cryoprotective effectively afforded to the endoexocellular formations and the membrane apparatus of the embryos concerned with uniform localization of the cryoprotectors in the mentioned domaines of the cryobiological system, this being due to different ability of cryoprotectors to permeate into the cells.

In a preferred embodiment of the invention the buffer-salt fluid contains a biologically potent substance. Application of such a substance adds much to the survival rate of the cells due to protection afforded to their cytoplasmic membrane against temperature shock and the 'solution effect'during the phase transition into ice. The biologically potent substance stabilizes the native structure of the cell membranes, thus ensuring against its damage in the course of recrystallization.

It is quite desireable that a choline-choloride solution be used as the biologically potent substance, which participates in the natural processes of methylation of the biologic structures and stablilizes the native membrane structure due to the presence of methyl groups.

According to one of the further embodiments of the present invention the choline-chloride solution is used in a 0.4 -percent concentration, which is concerned with the fact that a higher concentration will result in dis-turbed structural organization of the membranes due to surface-active properties of the aforesaid substance, whereas with a lower concentration of that substance it fails to exhibit the stabilizing effect mentioned above Further objects and advangtages of the present invention will become more apparent from a detailed description of some specific embodiments that follows.

BRIEF DESCRIPTION OF THE EMBODIMENTS

The method for low-temperature preservation of embryos comprise their cooling, with the aid of a refrigerant, down to the temperature of the latter, in a buffer-salt fluid. The cooling process is carried out in a temperature diffusive powdered material which has preliminary been cooled down to the refrigerant temperature. The buffer-salt fluid contains a mixture of the following cryoprotectors: glycerol, dimethylsulphoxide (DMSO), and a dihydric alcohol, as well as a biologically potent substance, e.g., a choline-chloride solution in a concentration of 0.4 percent.

Zinc may be used as the temperature diffusive powdered material.

1,2-propanediol may be used as dihydric alcohol.

When liquid nitrogen is used as the refrigerant, each of the three cryoprotectors is taken in a concentration of from 4.75 to 5.25 percent and in a ratio 1:1.

The method was carried into effect in cryopreservation of murine embryos which are at stage 32 of blastomeres.

Example 1

A total of 60 embryos were divided into six groups of ten embryos (in five drops in each group). Added to each of the groups were five drops of the Dulbecco's phosphate-salt fluid medium, containing 10.5 percent of glycerol, 10.6 percent of propyleneglycol, 10.5 percent of DMSO and 0.8 percent of choline-chloride, the concentration of each of the cryprotectos equalling 5.25 percent, and that of choline-chloride, 0.4 percent. All procedures were carried out at 4° C. Then the embryos in the fluid containing cryoprotectors were transferred to containers made of food packing foil, each measuring 1×1.5 cm, having a 0.1 ml capacity and a wall thickness of 0.03 mm. The free edges of the container were flared out and immersed for 10 seconds in a metallic vessel filled with powdered zinc cooled down to the temperature of liquid nitrogen. Then the containers were placed in liquid nitrogen to be stored there for three weeks, whereupon they were thawed in a water bath at 40° C. The survival rate of the thawed-out embryos equalled 94.2 percent as assessed against their development in a culture medium.

To substantiate the concentrate of the cryoprotectors, experiments were conducted similarly to Example 1, differing in the concentration of the cryoprotectors.

Survivability of the embryos was also determined by the data on thier development in a culture medium until the stage of blastocyst. The results of the experiment are tabulated in Table 1.

Growth of embryos during their cultivation after low-temperature preservation is calculated with respect to the growth of the same number of native embryos in Tables 1-5.

TABLE 1

Survival rate of embryos after their low-temperature preservation at various total concentrations of cryoprotectors

| Cryoprotector concentration, % | | | Survival rate of embryos, % |
|---|---|---|---|
| Glycerol | Propyleneglycol | DMSO | |
| 5.75 | 5.75 | 5.75 | 71.8 ± 1.45 |
| 5.5 | 5.5 | 5.5 | 85.4 ± 1.91 |
| 5.25 | 5.25 | 5.25 | 94.2 ± 0.62 |
| 5.0 | 5.0 | 5.0 | 94.8 ± 1.06 |
| 4.75 | 4.75 | 4.75 | 93.9 ± 0.18 |
| 4.5 | 4.5 | 4.5 | 86.6 ± 0.16 |
| 4.25 | 4.25 | 4.25 | 78.1 ± 1.2 |

It can be seen from Table 1 that the highest survival rate of the embryos is attained when the cryoprotectors are used in a concentration of from 4.75 to 5.25 percent (total concentration ranging within 14.25–15.75 percent).

Experiments similar to Example 1 were conducted for substantiating the ratio between the concentrations of the cryoprotectors in a cryoprotective medium, but the cryoprotectors were taken in the various ratios so that their total concentration in the cryoperservative was within 14.25 and 15.25 percent. The results are represented in Tables 2 to 4.

TABLE 2

Survival rate of embryos after their low-temperature preservation at various ratios between the cryoprotectors and at their total concentration of 15.75 percent

| Cryoprotector concentration, % | | | Survival rate of embryos, % |
|---|---|---|---|
| Glycerol | Propyleneglycol | DMSO | |
| 5.25 | 5.0 | 5.5 | 80.1 ± 1.16 |
| 5.0 | 5.25 | 5.5 | 83.2 ± 0.18 |
| 5.5 | 5.0 | 5.25 | 84.2 ± 2.18 |
| 5.0 | 5.5 | 5.25 | 83.4 ± 1.06 |
| 5.5 | 5.25 | 5.0 | 82.3 ± 1.06 |
| 5.25 | 5.5 | 5.0 | 82.2 ± 2.12 |

TABLE 3

Survival rate of embryos after their low-temperature preservation at various ratios between the cryoprotectors and at their total concentration of 15 percent

| Cryoprotector concentration, % | | | Survival rate of embryos, % |
|---|---|---|---|
| Glycerol | Propyleneglycol | DMSO | |
| 5.0 | 4.75 | 5.25 | 81.6 ± 1.42 |
| 4.75 | 5.0 | 5.25 | 80.1 ± 2.12 |
| 5.25 | 4.75 | 5.0 | 78.6 ± 0.19 |
| 4.75 | 5.25 | 5.0 | 79.8 ± 0.26 |
| 5.25 | 5.0 | 4.75 | 82.6 ± 1.21 |
| 5.0 | 5.25 | 4.75 | 83.5 ± 1.21 |

TABLE 4

Survival rate of embryos after their low-temperature preservation at various ratios between the cryoprotectors and at their total concentration of 14.25 percent

| Cryoprotector concentration, % | | | Survival rate of embryos, % |
|---|---|---|---|
| Glycerol | Propyleneglycol | DMSO | |
| 5.0 | 4.5 | 4.75 | 76.8 ± 2.14 |
| 4.5 | 5.0 | 4.75 | 74.9 ± 0.18 |
| 4.75 | 4.5 | 5.0 | 79.1 ± 1.28 |
| 4.5 | 4.75 | 5.0 | 81.3 ± 0.19 |
| 4.75 | 5.0 | 4.5 | 77.5 ± 0.26 |
| 5.0 | 4.75 | 4.5 | 79.6 ± 2.18 |

It is evident from Tables 2 to 4 that the survival rate of embryos drops in response to variation in the ratio between the percentage of the cryoprotectors in the freezing medium with their total concentration of 14.25 to 15.75 percent and an invariable percentage of choline-chloride (0.4 percent).

In order to substantiate the choline-chloride concentration the method was carried into effect as in Example 1 but the choline-chloride concentrations equalled 0.3 and 0.5 percent. The results are tablulated in Table 5.

TABLE 5

Survival rate of embryos after their low-temperature preservation vs concentration of choline-chloride and cryoprotectors in the cryopreservative

| Cryoprotectors concentration, % | | | Survival rate of embryos, % | |
|---|---|---|---|---|
| Glycerol | Propyleneglycol | DMSO | Choline chloride concentration of 0.3% | Choline-chloride concentration of 0.5% |
| 5.75 | 5.75 | 5.75 | 60.1 ± 1.18 | 65.3 ± 1.12 |
| 5.5 | 5.5 | 5.5 | 71.6 ± 2.19 | 76.2 ± 1.16 |
| 5.25 | 5.25 | 5.25 | 76.9 ± 1.04 | 84.6 ± 0.21 |
| 5.0 | 5.0 | 5.0 | 74.8 ± 0.86 | 72.1 ± 1.12 |
| 4.75 | 4.75 | 4.75 | 70.1 ± 0.91 | 68.9 ± 1.41 |
| 4.5 | 4.5 | 4.5 | 76.6 ± 0.36 | 69.5 ± 2.1 |
| 4.25 | 4.25 | 4.25 | 63.5 ± 1.18 | 54.2 ± 1.12 |

It is obvious from Table 5 that survivalrate of embryos is affected with the choline-chloride concentration above or below 0.4 percent.

EXAMPLE 2

The method was carried into effect as in Example 1, with the sole exception that used as the cryopreserving medium was the one employed in the prototype, i.e., the phosphate-salt fluid medium, containing 1.4 M glycerol and 1.1 M saccharose. In one case the embryos were frozen in containers made of food packing foil, while in the other case, in polystryene tubes. After thawing the percentages of the embryos that exhibited growth in a culture medium were 69.0 ±1.06 and 10.0 ±1.2, respectively. Hence high survival rate of embryos is attainable only when freezing in powdered zinc is carried out in the fluid medium according to the invention.

EXAMPLE 3

The method was carried into effect as in Example 1, with the exception that embryos were frozen in liquid nitrogen rather than in powdered zinc. Percentage of the embryos that developed in a culture medium after having been thawed out was 30.0 ±0.18. Hence high survival rate of embryos can be provided only when freezing is carried out in powdered zinc and in the fluid medium of the invention.

Thus the method of the invention makes it possible to increase the survival rate of the thawed-out embryos by 27.8 percent.

What is claimed is:

1. A method for cooling embryos to the temperature of a refrigerant in which they are to be stored comprising:
adding said embryos to a buffer-salt medium; said buffer-salt medium comprising a mixture of cryoprotectors, said cryoprotectors selected from the group consisting of glycerol, dimethylsulphoxide and a dihdric alcohol; placing said embryos in said buffer-salt medium into a container made of food packing foil; introducing said container with said embryos into a thermal diffusive powdered material; said powdered material having been cooled to the temperature of the refrigerant; said powdered material being a metal 2. A method as claimed in claim 1, wherein zinc is used as the thermal diffusive powdered material.

3. A method as claimed in claim 1, wherein the dihydric alcohol is 1,2-propanediol.

4. A method as claimed in claim 1, wherein liquid nitrogen is used as the refrigerant, and each of the three cryoprotectors is used in a concentration of from 4.75 to 5.52 percent.

5. A method as claimed in claim 1, wherein each of the three cryoprotectors is used in a 1:1 ratio.

6. A method as claimed in claim 1, wherein the buffer-salt fluid contains choline chlorine.

7. A method as claimed in claim 6 wherein the choline-chloride solution has a concentration of 0.4 percent.

* * * * *